US 11,510,834 B2

(12) United States Patent
Furuta

(10) Patent No.: US 11,510,834 B2
(45) Date of Patent: Nov. 29, 2022

(54) AUTOMATIC EXCRETION DISPOSAL DEVICE AND BUILDING

(71) Applicant: LIBERTYSOLUTION CO., LTD., Shimane (JP)

(72) Inventor: Miyuki Furuta, Matsue (JP)

(73) Assignee: LibertySolution Co., Ltd., Shimane (JP)

( * ) Notice: Subject to any disclaimer, the term of this patent is extended or adjusted under 35 U.S.C. 154(b) by 30 days.

(21) Appl. No.: 17/256,949

(22) PCT Filed: Sep. 13, 2019

(86) PCT No.: PCT/JP2019/036111
§ 371 (c)(1),
(2) Date: Dec. 29, 2020

(87) PCT Pub. No.: WO2020/261588
PCT Pub. Date: Dec. 30, 2020

(65) Prior Publication Data
US 2021/0290464 A1   Sep. 23, 2021

(30) Foreign Application Priority Data

Jun. 28, 2019 (JP) .............................. JP2019-121442

(51) Int. Cl.
*A61G 9/02* (2006.01)
*E03D 3/10* (2006.01)
(Continued)

(52) U.S. Cl.
CPC .................. *A61G 9/02* (2013.01); *E03C 1/01* (2013.01); *E03D 3/10* (2013.01); *E03D 5/024* (2013.01)

(58) Field of Classification Search
CPC .... E03D 9/10; E03D 5/01; E03D 3/10; E03D 2201/30; E03D 11/11; A61G 9/00–02
See application file for complete search history.

(56) References Cited

U.S. PATENT DOCUMENTS 5,245,710 A * 9/1993 Haselswerdt ............. E03D 9/10
4/435
2005/0055758 A1* 3/2005 Marston .................. E03D 11/11
4/321
(Continued)

FOREIGN PATENT DOCUMENTS

CN          104688403 A     6/2015
JP            3161991 U      4/2001
(Continued)

OTHER PUBLICATIONS

International Search Report for related PCT App No. PCT/JP2019/036111 dated Nov. 19, 2019, 2 pgs.
(Continued)

*Primary Examiner* — David P Angwin
*Assistant Examiner* — Nicholas A Ros
(74) *Attorney, Agent, or Firm* — Procopio, Cory, Hargreaves & Savitch LLP

(57) ABSTRACT

Provided is an automatic excretion disposal device (1) which is configured to automatically perform an excretion disposal of a person (P) to be cared, the device including: a cup (2) which is attached to a body of the person to be cared to receive excretion; a detection unit (3) which is configured to detect excretion in the cup; a feed water pipe which is configured to decompress cleaning water from a water supply (W) to a predetermined pressure and directly supplies the cleaning water, on the basis of detection result of the detection unit; a suction motor (30) which is configured to suck sewage generated when the body and inside of the cup are cleaned with the cleaning water supplied from the feed water pipe (R1), and to discharge the sewage to outside of the cup; a tank (10) which is configured to temporarily store the drainage sucked by the suction motor; and a drainage pump (20) which is configured to cause the drainage to forcibly flow out to a drainage piping connected to a sewer (Continued)

or a septic tank, while pulverizing solid matters contained in drainage in which the sewage stored in the tank is mixed with the cleaning water directly supplied from the feed water pipe.

4 Claims, 2 Drawing Sheets

(51) Int. Cl.
*E03C 1/01* (2006.01)
*E03D 5/02* (2006.01)

(56) References Cited

U.S. PATENT DOCUMENTS

| | | | |
|---|---|---|---|
| 2007/0044222 A1* | 3/2007 | Hedberg | A47K 11/04 4/321 |
| 2012/0233761 A1* | 9/2012 | Huang | A61F 5/442 4/458 |
| 2013/0036544 A1* | 2/2013 | Lee | A61G 9/003 4/443 |
| 2015/0328072 A1* | 11/2015 | Saitoh | A61F 5/441 4/457 |
| 2020/0040561 A1 | 2/2020 | Sugawara | |

FOREIGN PATENT DOCUMENTS

| | | | |
|---|---|---|---|
| JP | 3217681 U | 10/2001 | |
| JP | 2006055513 A | 3/2006 | |
| JP | 2008036018 * | 2/2008 | ............ A61G 9/02 |
| JP | 2008036018 A | 2/2008 | |
| JP | 2013523309 A | 6/2013 | |
| JP | 2013-212352 A | 10/2013 | |
| JP | 2016022367 A | 2/2016 | |
| JP | 2018096098 A | 6/2018 | |
| KR | 10-2008-0091916 A | 10/2008 | |
| WO | 2018139424 A1 | 8/2018 | |

OTHER PUBLICATIONS

Notice of Reasons for Rejection for related JP App No. 2019-121442 dated Sep. 3, 2019, 6 pgs.
Extended European Search Report dated Sep. 1, 2021 from EP Patent Application No. 19836449.9, 8 pages.
Notice of Allowance for Korean Application 10-2020-7002387. dated Feb. 8, 2022. pp. 3.

* cited by examiner

AUTOMATIC EXCRETION DISPOSAL DEVICE AND BUILDING

CROSS-REFERENCE TO RELATED APPLICATIONS

This application is a U.S. National Stage entry of PCT Application No; PCT/JP2019/036111 filed Sep. 13, 2019, which claims priority to Japanese Patent Application No. 2019-121442 filed Jun. 28, 2019, the contents of which are incorporated herein by reference.

TECHNICAL FIELD

The present invention relates to an automatic excretion disposal device and a building for automatically disposing of the excretions of persons to be eared for.

BACKGROUND ART

In recent years, the number of persons to be cared for, such as the elderly and physically handicapped persons, who require assistance in excretion disposal has increased year by year. While the number of persons to be cared for has increased, the number of nursing staff members engaged in nursing care is chronically insufficient. This trend is expected to become more significant in the future. Excretion disposal of persons to be cared for is most burdensome for nursing staff members. An automatic excretion disposal device has been proposed to assist with the excretions of such persons to be cared for and reduce the burden on nursing staff members.

The applicant has already proposed an automatic excretion disposal device which disposes of the excretions of a person to be cared for (see, for example, Patent Literature 1). This automatic excretion disposal device is equipped with a cup attached to the body of the person to be cared for, a suction unit which suctions the excretions into the cup, a sewage tank which stores the suctioned excretions, a cleaning unit which cleans the inside of the cup and the body, and a water supply tank which stores cleaning water and supplies the cleaning water to the cleaning unit. According to the automatic excretion disposal device described in Patent Literature 1, the body of the person to be cared for can be cleaned, and the excretions can be stored in the sewage tank after the disposal.

CITATION LIST

Patent Literature

Patent Literature 1

Japanese Unexamined Patent Application, First Publication No. 2016-022367

SUMMARY OF INVENTION

Technical Problem

However, even with the automatic excretion disposal device described in Patent Literature 1, since it is necessary to frequently supply water to the water supply tank, and it is necessary to frequently perform cleaning after discharging the sewage from the sewage tank, there is a need for the labor and time of the nursing staff member. In addition, according to the automatic excretion disposal device described in Patent Literature 1, some of the air of the interior air circulation is released to the atmosphere when suctioning excretions, and odor may leak into the living room. The inventors have further improved the automatic excretion disposal device under intensive research to further reduce the burden on nursing staff members and to prevent odor.

An object of the present invention is to provide an automatic excretion disposal device and a building capable of reducing an occurrence of odor, while significantly reducing the burden on nursing staff members.

Solution to Problem

In order to achieve the above object, the present invention provides an automatic excretion disposal device which is configured to automatically perform disposal of excretions of a person to be cared for, the device including: a cup which is attached to a body of the person to be cared for to receive excretions; a detection unit which is configured to detect excretion in the cup; a feed water pipe which is configured to decompress cleaning water from a water supply to a predetermined pressure and directly supplies the cleaning water, on the basis of a detection result of the detection unit; a suction motor which is configured to suck sewage generated when the body and an inside of the cup are cleaned with the cleaning water supplied from the feed water pipe, and to discharge the sewage outside of the cup: a tank which is configured to temporarily store the sewage sucked by the suction motor; a drainage pump which is configured to cause drainage to forcibly flow out to a drainage piping connected to a sewer or a septic tank, while pulverizing solid matter contained in drainage in which the sewage stored in the tank is mixed with the cleaning water directly supplied from the feed water pipe; an air supply pipe which is configured to supply air sucked by the suction motor to the cup; a branch pipe which is configured to branch from the middle of the air supply pipe and is connected to the drainage pipe; and a collecting unit which is configured to connect the branch pipe to the drainage pipe, exhausts a positive pressure air generated in the air supply pipe to the drainage pipe, and is formed to generate a back pressure which assists outflow of the drainage flowing out to the drainage pipe.

According to this invention, since the feed water pipe directly supplies the cleaning water from the water supply, an installation type water supply tank can be omitted to simplify a device configuration, and the burden on a nursing staff member can be significantly reduced. In addition, since the pressure of the cleaning water to be supplied from the water pipe is reduced to a predetermined pressure value suitable for circulation in the device, the device can be directly connected to the water pipe. In addition, since the drainage pump causes the drainage to directly flow out to a sewer or the like, while pulverizing the drainage, the installation type sewage tank can be omitted to simplify the device configuration, and the burden on the nursing staff member can be significantly reduced.

Further, according to the present invention, since the branch pipe branching from the air supply pipe is connected to the drainage pipe, it is possible to prevent odor from leaking into the living room of the person to be cared for and improve the living environment.

Furthermore, since the collecting unit is configured to generate a back pressure which assists the outflow of the sewage flowing out to the drainage pipe, using the flow of the air exhausted from the branch pipe, it is possible to smoothen the outflow of the drainage to the sewer.

Further, in the present invention, the suction motor may be configured to suck the inside of the cup, suck outside air from a gap generated between the cup and the body, cause the outside air to flow inside the air supply pipe, and prevent excretion and odor from leaking outside of the cup.

According to the present invention, it is possible to prevent the excretion and odor from leaking out, by sucking the outside air from the gap generated between the cup and the body, thereby improving the living environment.

Further, the present invention may be configured to further include a one-way valve that is provided in the middle of the drainage pipe connected to a downstream side of the drainage pipe and causes the drainage to flow in one direction.

According to the present invention, since the one-way valve is provided, even when the suction motor operates and the inside of the tank reaches a negative pressure, it is possible to prevent the drainage from flowing backward from the drainage pipe into the tank. In the device, although a one-way valve is used, it may be constituted by a motor valve or the like.

Further, the present invention may be a building which includes a piping connected to the water supply, a piping connected to the sewer, and the automatic excretion disposal device described above.

According to the present invention, if the building is provided with a piping connected to the water supply and a piping connected to the sewer, the automatic excretion disposal device can be installed, and it is possible to realize a nursing care facility which significantly reduces the burden on nursing staff member.

Advantageous Effects of Invention

According to the present invention, it is possible to reduce an occurrence of odor, while reducing the burden on nursing staff members.

DESCRIPTION OF EMBODIMENTS

Figure 1:
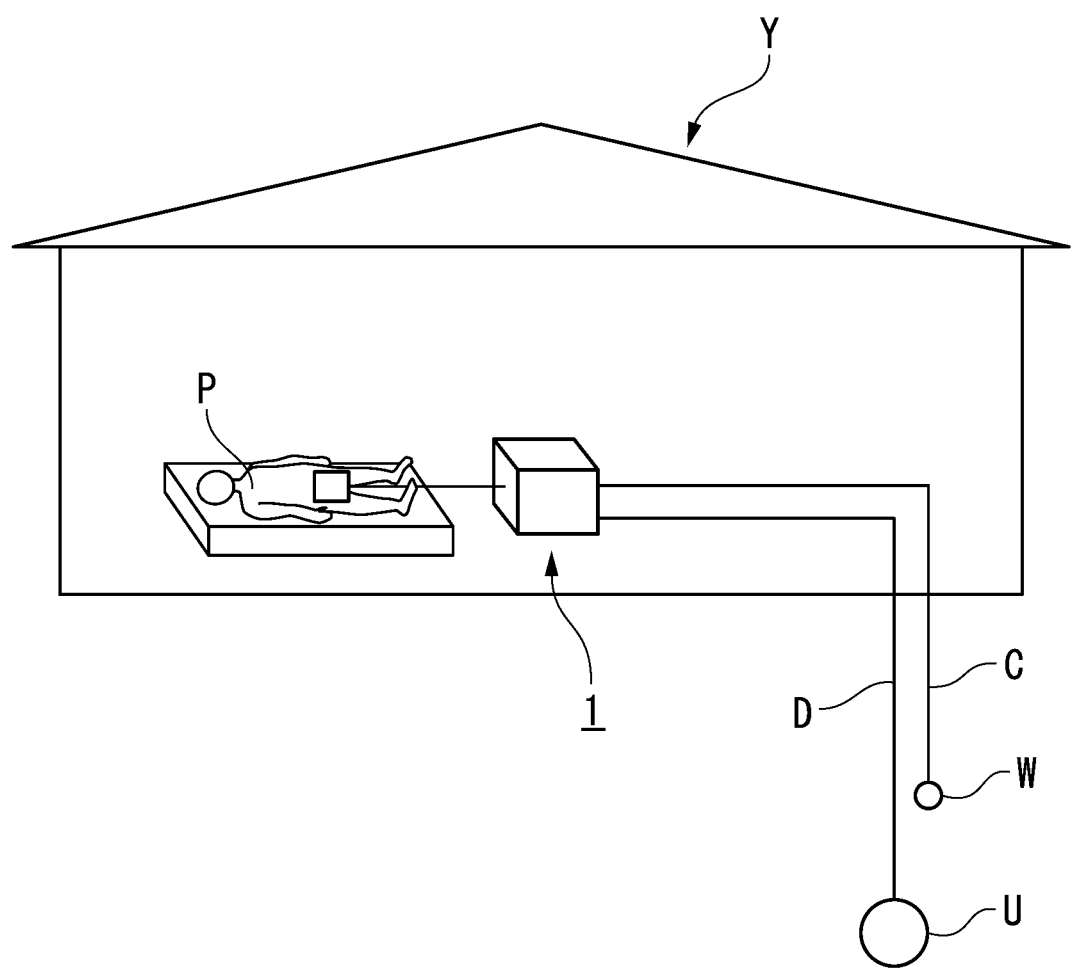
FIG. 1 is a diagram showing a configuration of a building in which an automatic excretion disposal device according to an embodiment of the present invention is installed.

Hereinafter, an embodiment of the automatic excretion disposal device according to the present invention will be described, while referring to the drawings.

As shown in FIG. 1, an automatic excretion disposal device 1 is a device which automatically performs excretion disposal, is installed inside a building Y provided with a piping C connected to a water supply W, and a piping D connected to a sewer U, and is configured to be directly supplied with water from the water supply W and to directly drainage sewage to the sewer U.

Figure 2:
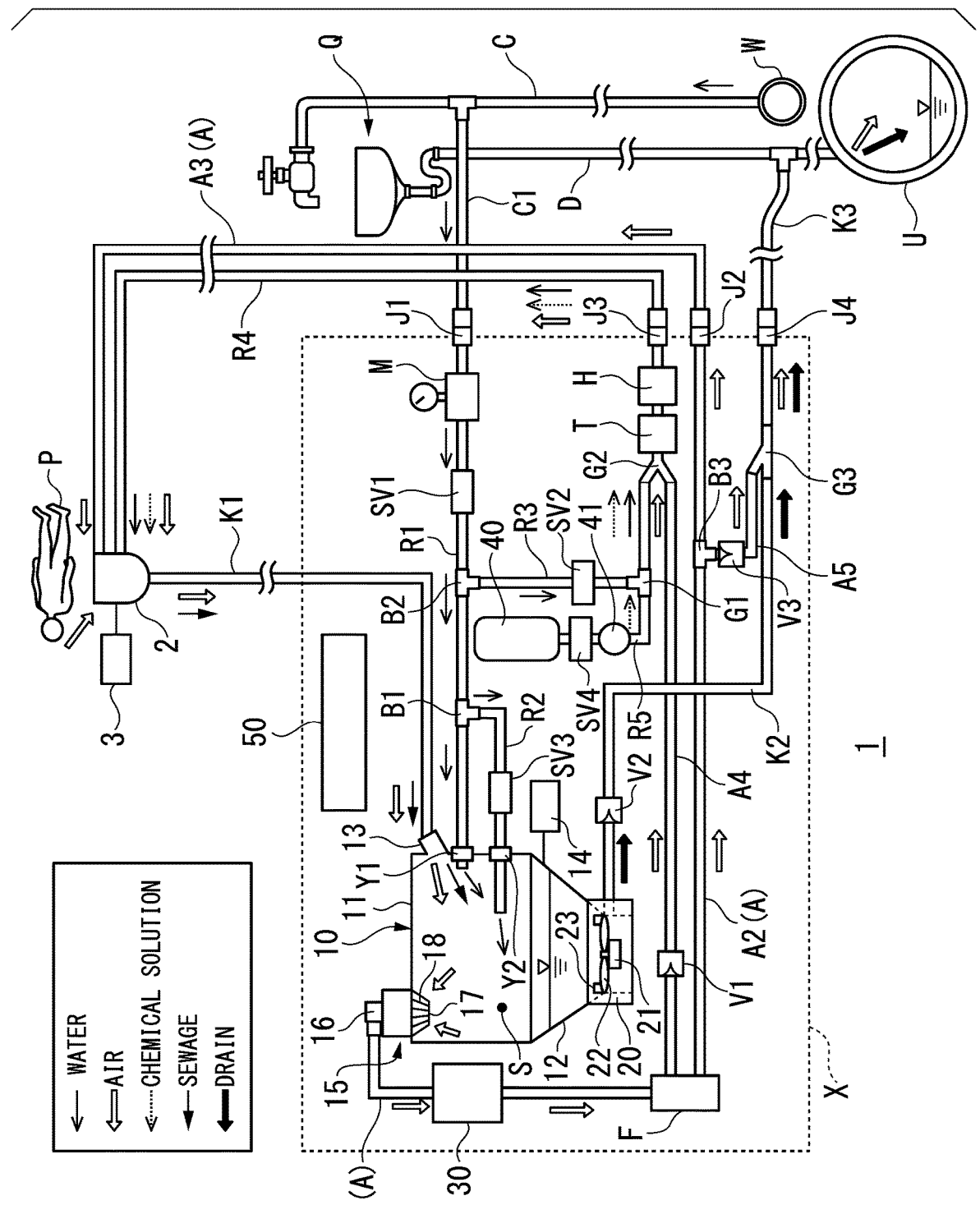
FIG. 2 is a diagram showing the configuration of the automatic excretion disposal device.

As shown in FIG. 2, for example, a piping C for the water supply W and a piping D for the sewer U connected to a wash basin Q are provided in a living room in which a person P to be cared stays. The pipings C and D may be connected to each of the water supply W and the sewer U, without being limited to the wash basin Q. Moreover, the sewer U may be a septic tank.

The automatic excretion disposal device 1 is equipped with a cup 2 attached to the body of the person P to be cared, a tank 10 which stores sewage containing excretion discharged from the inside of the cup 2, a drainage pump 20 which causes sewage to flow out to the sewer U from the tank 10, a suction motor 30 which causes excretion to flow into the tank 10 from the cup 2, a chemical solution tank 40 which stores the chemical solution to be supplied to the cup 2, and a control device 50 which performs overall control of excretion disposal. The components other than the cup 2 are housed in a housing X.

The cup 2 is formed to cover a region around the crotch of the person P to be cared (not shown). The detailed configuration such as the shape of the cup 2 is described, for example, in Patent Literature 1. The cup 2 has a contact part that comes into contact with the body of the person P to be cared. The contact part is formed of silicone resin, and improves the adhesion between the cup 2 and the body of the person P to be cared. The cup 2 temporarily receives excretion. Cleaning water is supplied to the cup 2 from the water supply W to clean the crotch or the like of the person P to be cared.

Air is supplied to the cup 2 as described below to dry the cleaned body of the person P to be cared and the inside of the cup 2. The cup 2 is provided with a detection unit 3 for detecting excretion. The detection unit 3 is a capacitance sensor that electrically detects whether the excretion is solid or liquid. A cycle of the excretion disposal of the automatic excretion disposal device 1 is started on the basis of the detection result of the detection unit 3.

The water supply W and the tank 10 are connected by a feed water pipe R1 via a branch piping C1 branching from the piping C. The branch piping C1 and the feed water pipe R1 are formed by, for example, a flexible hose. The branch piping C1 and the feed water pipe R1 are connected by a detachable hose joint J1. A pressure reducing valve M which adjusts the water pressure is connected to a downstream side of the hose joint J1. The pressure reducing valve M reduces the pressure of the cleaning water supplied from the branch piping C1 to a predetermined water pressure. The predetermined water pressure is set to a pressure value such that the pressure of the cleaning water is suitable for circulation in the automatic excretion disposal device 1. A solenoid valve SV1, which causes the decompressed cleaning water to flow or blocks it, is provided on the downstream side of the pressure reducing valve M.

The solenoid valve SV1 enters an ON-state after it is determined that excretions have been detected in the cup 2 by the detection unit 3 as described below, and supplies the cleaning water from the water supply W into the automatic excretion disposal device 1. The solenoid valve SV1 keeps the ON-state during an operation state of one cycle of the excretion disposal of the automatic excretion disposal device 1, and enters an OFF-state at the time when one cycle is completed. A feed water pipe R1 is connected to the tank 10 via a connection part Y1 on the downstream side of the solenoid valve SV1. The feed water pipe R1 supplies cleaning water to the tank 10 during one cycle of the excretion disposal, and cleans a predetermined region of the tank 10.

The feed water pipe R1 branches at a branch part B1 on the upstream side of the connection part Y1. A branch pipe R2 branching from the feed water pipe R1 is connected to a connection part Y2 different from the connection part of the feed water pipe R1. The branch pipe R2 supplies cleaning water to a region different from the region in the tank 10 that is cleaned with the cleaning water to be supplied from the feed water pipe R1. The cleaning effect in the tank 10 is enhanced by the feed water pipe R1 and the branch pipe R2.

The branch pipe R2 is provided with a solenoid valve SV3 between the connection part Y2 and the branch part B1. After it is determined that excretion is detected in the cup 2, the solenoid valve SV3 repeats entering the ON-state and the OFF-state at predetermined time intervals in one cycle of the excretion disposal. After it is determined that the solid excretion is detected in the cup 2, the solenoid valve SV3 repeats a cycle during which an OFF-state is set for 5 seconds and then an ON-state is set for 10 seconds three times, and cleans the tank 10. After it is determined that liquid excretion is detected in the cup 2, the solenoid valve SV3 repeats a cycle during which an OFF-state is set for 5 seconds and then an ON-state is set for 10 seconds twice, and cleans the tank 10. The time flow of the solenoid valve SV3 can be changed by a program.

The tank 10 is a container which temporarily stores sewage. The tank 10 and the cup 2 are connected by a sewage piping K1 to be described below for sewage disposal. The tank 10 is equipped with an air chamber 11 into which air enters, and a storage unit 12 provided below the air chamber 11. The air chamber 11 has a closed space S formed therein. The storage unit 12 is formed such that the diameter decreases downward. The storage unit 12 is provided with a detection unit 14 that detects a water level of the sewage.

A drainage pump 20 is provided below the storage unit 12. A drainage pipe K2 which causes the drainage to flow out is connected to the downstream side of the drainage pump 20. The drainage pipe K2 is connected to a piping K3 via a hose joint J4. The piping K3 is formed by a flexible hose. The piping K3 is connected to a piping D for the sewer U.

The drainage pump 20 is equipped with a rotary vane 22 on which a pulverizing cutter 23 to be driven by a motor 21 is formed. As the motor 21, for example, a waterproof DC brushless motor is used. As the motor 21, any other motor that generates a rotational driving force, such as a DC brush motor or an AC motor, may be used, in addition to a DC brushless motor. The drainage pump 20 causes the solid matters contained in the drainage, in which the cleaning water directly supplied from the water supply W is mixed with the sewage, to forcibly flow out to the drainage pipe K2 connected to the sewer U, while finely pulverizing the solid matters with the pulverizing cutler 23 by the rotation of the rotary vanes 22.

A one-way valve V2 which causes the drainage to flow to the sewer U side in one direction is provided in the middle of the drainage pipe K2. The one-way valve V2 prevents backflow from the drainage pipe K2 when the suction motor 30 operates as described below. In the drainage pipe K2, a collecting unit G3 in which a branch pipe A5 to be described below joins is provided on the downstream side of the one-way valve V2. When the detection unit 14 detects that the drainage in which the sewage and the cleaning water stored in the storage unit 12 are mixed has a predetermined water level, the drainage pump 20 causes the drainage to flow out of the tank 10.

The air chamber 11 is provided with connection parts Y1 and Y2. The air chamber 11 and the sewage piping K1 are connected via the suction port 13. The air chamber 11 is connected to a suction motor 30 that sucks air into the space S via a piping A1. A separation device 15 which separates sewage and air is provided at a connection part between the piping A1 and the air chamber 11. The separation device 15 is provided with an air turbine motor 16 that provides a rotational driving force, and a rotary blade 17 that is rotated by the air turbine motor 16. The rotary blade 17 is equipped with a plurality of blades 18 formed radially from a rotary shaft. The air turbine motor 16 is driven by the suction pressure of the suction motor 30. The suction motor 30 may be of any type that generates a rotational driving force, such as a DC brush motor or an AC motor, in addition to a DC brushless motor.

When the suction motor 30 operates to suck the air into the space S, the air turbine motor 16 is operated by the passing air and rotates the rotary blade 17. Then, the sewage adhering to the blade 18 of the rotary blade 17 is blown into the air chamber 11 by a centrifugal force, and only air is sucked from a gap between the plurality of blades 18. The suction motor 30 enters the ON-slate in one cycle of the excretion disposal after it is determined that excretion is detected in the cup 2. A method other than the air turbine motor 16 may be used for separating air and dirt.

After the solenoid valves SV1 to SV4 stop and the cleaning mode ends, the suction motor 30 operates for 15 seconds to enter a drying mode, and supplies air to the cup 2 to dry the inside of the cup 2 and the body of the person P to be cared. The air sucked by the suction motor 30 flows into a piping A2 that communicates with the outside of the housing X via an air filter F connected to the downstream side of the suction motor 30. The time flow of the suction motor 30 can be changed by a program.

The air filter F removes fine particles and an odor of sewage mixed into the air flowing through the piping A1 with activated carbon or the like. Since the separation device 15 operates, the air filter F is rarely contaminated. The piping A2 connected to the downstream side of the air filter F is connected to an air piping A3 communicating with the cup 2 via a detachable hose joint J2 provided on the housing X.

The air supply pipe A is constituted by the piping A1, the piping A2, and the air piping A3. In the piping A2, a branch pipe A5 is connected between the air filter F and the hose joint J2 via a branch part B3. The downstream side of the branch pipe A5 is connected to the drainage pipe K2 via the collecting unit G3.

A one-way valve V3 is provided between the branch part B3 of the branch pipe A5 and the collecting unit G3. The one-way valve V3 causes air to flow in one direction from the branch part B3 side to the collecting unit G3 side in the branch tube A5, and prevents inflow of drainage from the drainage pipe K2 to the branch part B3 side.

Further, the collecting unit G3 connects the branch pipe A5 and the drainage pipe K2, and is formed so that a flow line direction of the air flowing through the branch pipe A5 matches a streamline direction of the drainage flowing through the drainage pipe K2. As a result, the collecting unit G3 exhausts air having a positive pressure generated in the piping A2 to the drainage pipe K2 and generates an airflow on the downstream side of the collecting unit G3, thereby generating a back pressure for assisting the outflow of drainage flowing out to the drainage pipe K2. Due to the back pressure generated by the branch pipe A5, the drainage staying between the one-way valve V2 and the collecting unit G3 in the drainage pipe K2 easily flows out to the downstream side.

The branch pipe A5 releases a positive pressure with respect to atmospheric pressure generated in the piping A2 by the outside air sucked by the suction motor 30 to the drainage pipe K2 as described below, and adjusts the pressure in the piping A2. The air containing odor is exhausted to the sewer U without being released to the atmosphere by the branch pipe A5. Therefore, the odor in the living room in which the person P to be cared stays is reduced by the branch pipe A5.

The air piping A3 connected to the piping A2 is a piping which supplies air into the cup 2. The air piping A3 is formed by a flexible hose. The air supplied from the air piping A3 dries the pubic area and the anus of the person P to be cared after cleaning, as described below. The air supplied into the cup 2 is sucked into the tank 10 by the suction motor 30 through the sewage piping K1. Therefore, the air is basically circulated by the suction motor 30 through the tank 10. the piping A1, the piping A2, the air piping A3, the cup 2, the sewage piping K1, and the tank 10 in this order.

The suction motor 30 generates a negative pressure for sucking the inside of the cup. Although it is desirable that the cup 2 and the body of the person P to be cared are completely in close contact with each other, a gap may be generated therebetween depending on conditions such as the posture of the person P to be cared and individual differences. The suction motor 30 sucks outside air from a gap generated between the cup 2 and the body of the person P to be cared. This prevents excretion and odor from leaking out of the cup 2 from the gap generated between the cup 2 and the body of the person P to be cared.

A water conveyance piping R4 is connected to the cup 2 to supply the cleaning water to the cup 2. The water conveyance piping R4 is connected to a feed water branch pipe R3 branching from the feed water pipe R1 via the hose joint J3 provided in the housing X.

The feed water branch pipe R3 branches from a branch part B2 between the solenoid valve SV1 and the branch part B1 in the feed water pipe R1. A solenoid valve SV2 is provided on the downstream side of the branch part B2. The solenoid valve SV2 controls the supply of the cleaning water to the cup 2. The solenoid valve SV2 starts operating in conjunction with the solenoid valve SV1 and the suction motor 30. The solenoid valve SV2 repeats the ON-state and the OFF-state in a predetermined cycle in one cycle of the excretion disposal.

After it is determined that solid excretion is detected in the cup 2, the solenoid valve SV2 repeats a cycle during which an ON-state is set for 5 seconds and then an OFF-state is set for 10 seconds three times, and intermittently supplies the cleaning water to the cup 2. After it is determined that liquid excretion is detected in the cup 2, the solenoid valve SV2 repeats a cycle during which an ON-state is set for 5 seconds and then an OFF-state is set for 10 seconds twice, and intermittently supplies the cleaning water to the cup 2. That is, the solenoid valve SV2 performs an operation opposite to that of the solenoid valve SV3 of the branch pipe R2 connected to the tank 10. The time flow of the solenoid valve SV2 can be changed by a program.

At a joining part G1 on the downstream side of the solenoid valve SV2, the feed water branch pipe R3 joins the pipe R5 to which the chemical solution is supplied. A chemical solution is supplied from the chemical solution tank 40 to the pipe R5. The chemical solution is, for example, an aqueous solution harmless to the human body, in which an agent having a bactericidal action such as aqueous hypochlorous acid and a deodorant are mixed. A solenoid valve SV4 and a chemical solution injection pump 41 for sending the chemical solution are provided between the chemical solution tank 40 and the joining part G1. The chemical solution tank 40 stores a predetermined volume of the chemical solution. The chemical solution is replenished as appropriate. The chemical solution tank 40 may be a drop type or a suction type.

The solenoid valve SV4 operates in conjunction with the solenoid valve SV2. The chemical solution injection pump 41 discharges a predetermined amount (for example, 20 [cc]) of chemical solution in conjunction with the ON-state of the solenoid valve SV4. The chemical solution discharged from the chemical solution injection pump 41 is mixed with the cleaning water at the joining part G1 and diluted to have a predetermined chlorine concentration (for example, 30 [ppm] or more). The feed water branch pipe R3 through which the cleaning water mixed with the chemical solution flows, joins the piping A4 to which air is supplied, at a joining part G2 on the downstream side of the joining part G1.

The upstream side of the piping A4 is connected to the air filter F, and the downstream side thereof is connected to the joining part G2. A one-way valve V1 for preventing backflow is provided in the middle of the piping A4. The one-way valve V1 prevents the cleaning water from flowing into the air filter F side. The cleaning water mixed with the chemical solution is mixed with air at the joining part G2 to improve the cleaning effect. The cleaning water is supplied to the downstream side via a pressure switch T provided on the downstream side of the joining part G2.

The pressure switch T is turned off when the internal pressure of the apparatus becomes equal to or higher than a predetermined pressure due to clogging of the path to the cup 2 and bending, and the pressure switch T is turned on when the internal pressure becomes less than the predetermined pressure. For example, when the solenoid valves SV1 and SV2 are in a water supply state of the ON-state, if the pressure reaches a predetermined pressure or higher, the pressure switch T turns off the solenoid valve SV2 and stops the water feed. A heater H is provided on the downstream side of the pressure switch T. The heater H heats the cleaning water to a predetermined temperature so that the person P to be cared does not become uncomfortable when the body of the person P to be cared is cleaned with the cleaning water. The heater H is formed by, for example, an electrically heated ceramic type.

The heater H operates in conjunction with the operation of the ON-state of the solenoid valve SV2. The cleaning water having passed through the heater H flows into the water conveyance piping R4 via the hose joint J3. Thereafter, the cleaning water is supplied into the cup 2 through the water conveyance piping R4. The cleaning water cleans the body of the person P to be cared in the cup 2 and also cleans the excretion in the cup 2. The solid excretion is mixed with the cleaning water to be softened or pulverized to improve the fluidity.

The sewage in which the excretion and the cleaning water are mixed is discharged out of the cup 2 by the suction force generated by the suction motor 30. The sewage flows through the sewage piping K1 and is injected from the suction port 13 into the air chamber 11 in the tank 10. The sewage falls in the air chamber 11 and is stored in the storage unit 12. The cleaning water and sewage supplied from the feed water pipe R1 and the branch pipe R2 are mixed and stored in the storage unit 12. As described above, when the water level of the storage unit 12 reaches a predetermined value by the detection unit 14, the drainage in which the cleaning water and the sewage are mixed flows out to the sewer U by the drainage pump 20.

When one cycle of the excretion disposal is completed and then the detection unit 3 detects the excretion remaining in the cup 2, one cycle of the excretion disposal is repeatedly executed.

The control device 50 comprehensively controls at least one or more configurations of the solenoid valves SV1 to SV4, the separation device 15, the drainage pump 20, the suction motor 30, the chemical solution injection pump 41, and the heater H, and executes a cycle of the excretion disposal. The control device 50 is realized by executing a program (software) through a processor such as a Central Disposing Unit (CPU). Some or all of the respective functional units may be realized by hardware such as a large Scale Integration (LSI), an Application Specific Integrated Circuit (ASIC), a Field-Programmable Gate Array (FPGA), or may be realized by cooperation of software and hardware.

Each of the solenoid valves SV1 to SV4, the separation device 15, the drainage pump 20, the suction motor 30, the chemical solution injection pump 41, and the heater H may be controlled by the control device 50, or may operate to be interlocked with each configuration. In addition, the automatic excretion disposal device 1 is equipped with a power supply unit (not shown) to which electric power is supplied, a safety device (not shown) for stopping operation when an overload or water leakage occurs, and the like.

As described above, according to the automatic excretion disposal device 1, since the cleaning water is directly supplied from the water supply, an installation type water supply tank can be omitted to simplify and downsize the device. Further, the labor for replenishing the cleaning water to installation type water supply tank can be omitted, and the burden on the nursing staff member can be significantly reduced. In addition, according to the automatic excretion disposal device 1, since the drainage is made to directly flow out from the tank 10 to the sewer, the installation type sewage tank can be omitted to simplify and downsize the devices, and the labor for cleaning the installation type sewage tank can be omitted, and the burden on nursing staff member can be significantly reduced. Further, according to the automatic excretion disposal device 1, by discharging some of the air circulating in the device to the sewer, odor leakage can be significantly reduced, and the living environment of the person P to be cared can be made comfortable.

Although an embodiment of the present invention has been described above, the present invention is not limited to the above-described embodiment, and can be appropriately changed without departing from the gist of the embodiment. For example, when clogging occurs in the piping K3 connected to the sewer, the clogging of the piping K3 may be eliminated by adjusting the flow rate of the air flowing through the branch pipe A5 to increase. Further, hot water may be supplied from the piping C.

REFERENCE SIGNS LIST

1 Automatic excretion disposal device
2 Cup
3 Detection unit
10 Tank
11 Air chamber
12 Storage unit
13 Suction port
14 Detection unit
15 Separation device
16 Air turbine motor
17 Rotary blade
18 Blade
20 Drainage pump
21 Motor
22 Rotary vane
23 Pulverizing cutter
30 Suction motor
40 Chemical solution tank
41 Chemical solution injection pump
50 Control device
A Air supply pipe
A1 Piping
A2 Piping
A3 Air piping
A4 Piping
A5 Branch pipe
B Branch part
B1 Branch part
B2 Branch part
B3 Branch part
C Piping
C1 Branch pipe
D Piping
F Air filter
G1 Joining part
G2 Joining part
G3 Collecting unit
H Heater
J1 to J4 Hose joint
K1 Sewage piping
K2 Drainage Pipe
K3 Piping
M Pressure reducing valve
P Person to be cared
Q Wash basin
R1 Feed water pipe
R2 Branch pipe
R3 Feed water branch pipe
R4 Water conveyance piping
R5 Piping
S Space
SV1 to SV4 Solenoid valve
T Pressure switch
U Sewer
V1 to V3 One-way valve
W Water supply
X Housing
Y Building
Y1, Y2 Connection part

The invention claimed is:

1. An automatic excretion disposal device which is configured to automatically perform an excretion disposal of a person to be cared, the device comprising:
a cup which is attached to a body of the person to be cared to receive excretion;
a detection unit which is configured to detect excretion in the cup;
a feed water pipe which is configured to decompress cleaning water from a water supply to a predetermined pressure and directly supplies the cleaning water, on a basis of a detection result of the detection unit;
a suction motor which is configured to suck sewage generated with the excretion and the cleaning water supplied from the feed water pipe when the body and an inside of the cup are cleaned with the cleaning water, and to discharge the sewage to outside of the cup;
a tank which is configured to temporarily store the sewage sucked by the suction motor;

a drainage pump which is configured to cause drainage to forcibly flow out to a drainage piping connected to a sewer or a septic tank, while pulverizing solid matters contained in the drainage, wherein the drainage is a mixture of the sewage stored in the tank and the cleaning water directly supplied from the feed water pipe;

an air supply pipe which is configured to supply air sucked by the suction motor to the cup;

a branch pipe which is configured to branch from a middle of the air supply pipe and is connected to the drainage pipe; and a collecting unit which is configured to connect the branch pipe and the drainage pipe, exhausts a positive pressure air generated in the air supply pipe to the drainage pipe, and is formed to generate a back pressure which assists outflow of the drainage flowing out to the drainage pipe.

2. The automatic excretion disposal device according to claim 1, wherein the suction motor is configured to suck inside of the cup, sucks outside air from a gap generated between the cup and the body, to cause the outside air to flow inside the air supply pipe, and to prevent excretion and odor from leaking to outside of the cup.

3. The automatic excretion disposal device according to claim 1, further comprising:

a one-way valve provided in a middle of the drainage pipe connected to a downstream side of the drainage pipe to cause the drainage to flow in one direction.

4. A building comprising:

a piping connected to a water supply to a predetermined pressure and directly supplies the cleaning water;

a piping connected to a sewer; and the automatic excretion disposal device according to claim 1.

* * * * *